United States Patent

Muñiz et al.

[11] Patent Number: 5,239,985
[45] Date of Patent: Aug. 31, 1993

[54] ELECTRODE TO DESTROY RENAL STONES

[75] Inventors: Manuel S. Muñiz; Juan R. Zamora; Berto O. H. Gutierrez, all of Havana, Cuba

[73] Assignee: Medicuba, Havana, Cuba

[21] Appl. No.: 870,211

[22] Filed: Apr. 16, 1992

Related U.S. Application Data

[63] Continuation of Ser. No. 611,468, Nov. 6, 1990, abandoned, which is a continuation of Ser. No. 186,616, Apr. 27, 1988, abandoned.

[30] Foreign Application Priority Data

Apr. 28, 1987 [CU] Cuba ......................................... 65/87

[51] Int. Cl.$^5$ ............................................. A61B 17/22
[52] U.S. Cl. ................. 128/24 EL; 606/128; 367/147
[58] Field of Search ........ 128/24 AA, 24 EL, 660.03, 128/639; 606/128; 367/147

[56] References Cited

U.S. PATENT DOCUMENTS

| 2,559,227 | 7/1951 | Rieber | 128/24 A |
| 4,608,983 | 9/1986 | Muller et al. | 128/328 |

FOREIGN PATENT DOCUMENTS 2635635  2/1978  Fed. Rep. of Germany ...... 128/328

Primary Examiner—Ruth S. Smith
Attorney, Agent, or Firm—Lackenbach Siegel Marzullo Aronson & Greenspan

[57] ABSTRACT

A medical electrode arrangement for urological use, has a core with an aperture going therethrough. This aperture receives a first electrode. A cage is defined by at least a side wall having first and second ends. The first end has a receiving unit for receiving a second electrode. An inner space of said cage is situated between the first and second ends and is surrounded by the side wall. The inner space is adapted to receive the core with a first electrode and a second electrode. A plurality of openings penetrating through the side wall of the core and extend from the first end toward the second end.

1 Claim, 1 Drawing Sheet

ELECTRODE TO DESTROY RENAL STONES

This is a continuation of Ser. No. 611,468; filed Nov. 6, 1990 now abandoned which is a continuation of Ser. No. 186,616, filed Apr. 27, 1988 now abandoned.

FIELD OF THE INVENTION

This invention relates to medical electrodes and more particularly to medical electrodes which operation is based on creation of shock waves adapted to destroy renal stones.

BACKGROUND OF THE INVENTION

There are many types of medical electrodes known in the industry.

One of such electrodes is described in U.S. Pat. No. 3,150,430. A typical medical electrode usually consists of a core with a rigid sharp end and a socket with a central aperture. Six electrode apertures are situated at the perimeter thereof and have center lines which are parallel to a center line of the central aperture. A cage of the electrode is an additional component of the socket formed by six elements welded to hold an apex.

A technical drawback of this electrode is that it is not interchangeable and can be used only once.

Another electrode is described in German Patent 3316837. This electrode consists of a cage formed by three elements that support a mandrel. An apex is placed in a cylindrical shaped bar and is changeable and adjustable. A core which ends in the mandrel holds the apex.

The mass of the mandrel causes increase in kinetic moment which results in the increase of the stresses in the elements supporting the mandrel. This decreases the life span and reliability of the electrode. Manufacturing of such electrodes is complex and their use leads to a significant loss of energy.

DESCRIPTION OF THE PREFERRED EMBODIMENT

Figure 1:
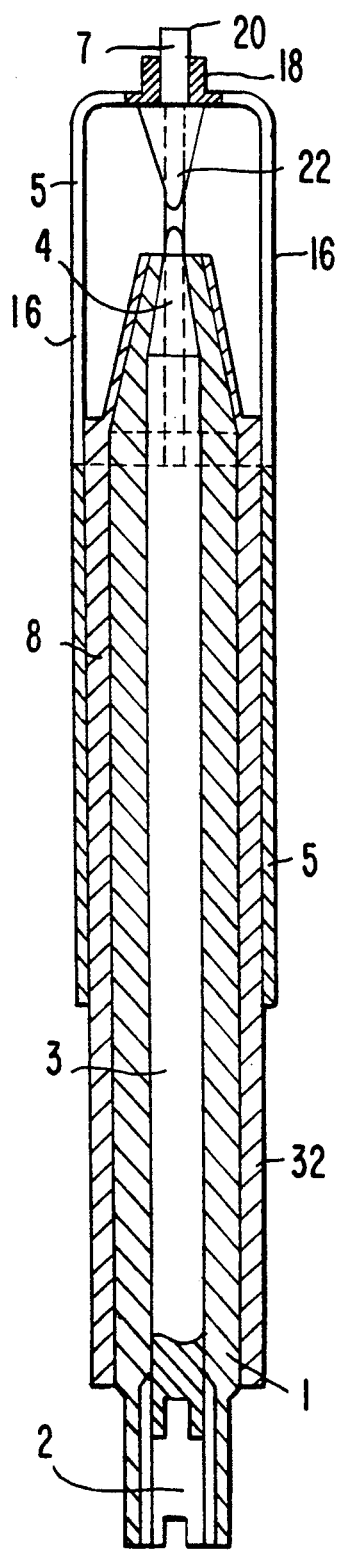
FIG. 1 shows a partially cross-sectional view of the electrode in the assembled condition.

Referring now to FIG. 1 where an electrode assembly according to the present invention is best shown. The assembly consists of a core 1 with an outside surface 8 and a threaded aperture 2 which goes therethrough. A first electrode 3 is provided with a first end 4 of substantially conical configuration which can be welded to the electrode.

Figure 2:
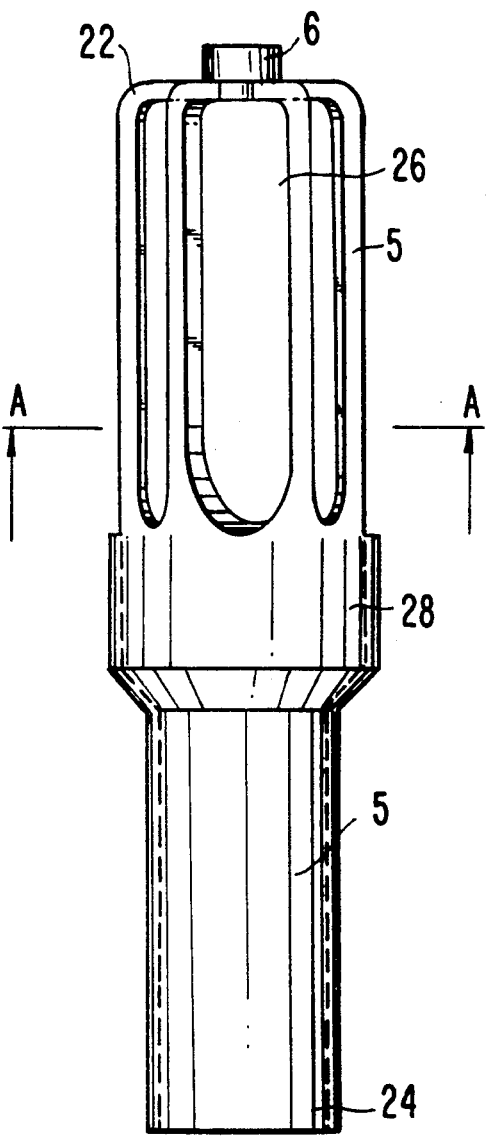
FIG. 2 shows a partially perspective view of the cage.

It is also shown in FIG. 1 that an interchangeable cage 5 consists of identical arms 16 extending from a central element 18 having a central aperture 6. A second electrode 7 is provided with an elongated part 20 and a conical part 22. The second electrode 7 is connected to the cage in such a manner that its elongated part 20 engages the central aperture 6 and the second conical end 22 faces the first conical end 4 of the first electrode. It is illustrated in FIG. 1 that the outside surface 8 of the core is received within the arms 16 of the cage. In the assembled condition of the electrode (see FIG. 1), the arms 16 extend substantially along the length of the core. In another form of the cage illustrated in FIG. 2 an upper part 22 and a lower part 24 are shown. The central element 18 having the central aperture 6 is situated at a top of the upper part 22. A plurality of arms in general and four arms 16 in particular extend outwardly and downwardly from the central element. It is shown in FIG. 2 that a plurality of elongated side openings 26 extending downwardly from the central part 18 separate the arms 16 from each other. The side openings do not extend through the entire length of the upper part and a solid connecting part 28 connects the upper part 22 and the lower part 24.

It is shown in FIG. 1 that an outer sleeve 32 covers an outside surface of the core or central element 8.

It is shown in FIG. 1 that a diameter of the elongated part 20 of the second electrode 7 is smaller than the base of the conical part 22. In view of that, portions of the base extend outwardly from the cylindrical elongated part 20 to define shoulders. According to FIG. 1, such shoulders has a straight-lined configurations.

It is also illustrated in FIG. 1 that the interior surface of the central element 18 has a flat, straight-lined configuration. In the assembled condition of the present invention, the substantially flat shoulders engage the substantially flat interior surface of the central element, preventing the second electrode from being withdrawn from the cage and stabilizing positioning of the second electrode within the central element 18.

Figure 3:
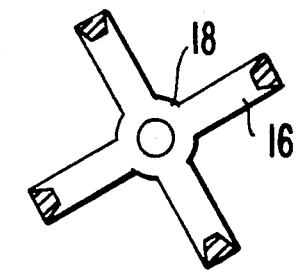
FIG. 3 shows a view according to the sectional line A—A of FIG. 2.

FIG. 3 illustrates that in the area of connection between the central element 18 and the arms, each two adjacent arms are positioned to each other at an angle of approximately 90°.

FIG. 1 shows that in the assembled condition of the electrode arrangement the conical part or a tip 4 of the first electrode and the conical part or a tip 22 of the second electrode face each other within the inner space of the cage at a level of the openings 26.

Therefore, during use of the assembly impulses or waves generated as a result of the operation of electrodes penetrate beyond the assembly substantially through the openings 26 within the cage.

What is claimed:

1. A medical electrode assembly for use in apparatus for destroying renal stones, comprising:
   an outer tubular sleeve having a conical end portion and an open end portion;
   a first conductive electrode having a longitudinal axis;
   a core member in the outer sleeve extending coaxially therewith and having an open end portion and a conical part complimentary with said conical end portion of the tubular sleeve, said core having an axial bore for receiving said first conductive electrode;
   said first conductive electrode extending in said bore along said longitudinal axis and having a conical tip at one end, a slot situated at an opposite end thereof, said conical tip extending outwardly of the conical end part of the core;
   a cage mounted on said outer sleeve, said cage having a solid tubular member with an interior part engaging said outer sleeve, said cage having four arms spaced circumferentially from each other and extending coaxially away from said solid tubular member, ends of said arms remote from said tubular member being bent inwardly and joined together to define a receiving portion, said receiving portion having a substantially flat interior part facing said first electrode and a central aperture coaxial with said longitudinal axis of said first electrode;

a second conductive electrode having a conical tip with a base and a substantially cylindrical engaging portion, said second conductive electrode engaging said central aperture, said base of the conical tip being substantially larger than a diameter of the cylinder of the engaging portion, so that parts of said base extend outwardly from said cylindrical engaging portion to define substantially flat shoulders, said substantially flat shoulders engaging said substantially flat interior part of the receiving portion to stabilize positioning of said second electrode within said receiving portion;

said second conductive electrode extending into said tubular cage and having its conical tip axially juxtaposed to the conical tip of said first electrode and separated therefrom by a gap.

* * * * *